(12) United States Patent
Lai et al.

(10) Patent No.: US 7,182,914 B2
(45) Date of Patent: Feb. 27, 2007

(54) STRUCTURE AND MANUFACTURING PROCESS OF A NANO DEVICE TRANSISTOR FOR A BIOSENSOR

(75) Inventors: Ming-Jiunn Lai, Hsinchu (TW);
Hung-Hsiang Wang, Hsinchu (TW);
Jeng-Hua Wei, Hsinchu (TW);
Hsin-Hui Chen, Hsinchu (TW);
Ming-Jer Kao, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 193 days.

(21) Appl. No.: 10/721,876

(22) Filed: Nov. 26, 2003

(65) Prior Publication Data

US 2005/0045875 A1 Mar. 3, 2005

(30) Foreign Application Priority Data

Aug. 26, 2003 (TW) .............................. 92123497 A (51) Int. Cl.
*B32B 5/02* (2006.01)
*B32B 27/04* (2006.01)
*B32B 27/12* (2006.01)
*G01N 27/00* (2006.01)

(52) U.S. Cl. ............... 422/82.01; 257/27; 257/288; 324/769; 422/50; 422/68.1; 422/82.02; 435/287.1; 435/287.2; 435/287.9; 436/518; 436/524; 436/149

(58) Field of Classification Search ................. 435/4, 435/6, 7.1, 287.1–287.2, 287.9, 288.3; 436/518, 436/524, 149; 422/50, 68.1, 82.01, 82.02; 257/27, 253, 288; 324/769; 327/203, 206, 327/208, 389
See application file for complete search history.

(56) References Cited

U.S. PATENT DOCUMENTS

| | | | | |
|---|---|---|---|---|
| 4,238,757 A | * | 12/1980 | Schenck | 257/253 |
| 5,066,582 A | * | 11/1991 | Tsuruta et al. | 435/7.1 |
| 5,309,085 A | * | 5/1994 | Sohn | 257/253 |
| 6,482,639 B2 | * | 11/2002 | Snow et al. | 435/287.2 |
| 6,627,154 B1 | * | 9/2003 | Goodman et al. | 422/82.01 |
| 6,716,642 B1 | * | 4/2004 | Wu et al. | 436/518 |
| 2004/0262636 A1 | * | 12/2004 | Yang et al. | 257/200 |
| 2005/0053524 A1 | * | 3/2005 | Keersmaecker et al. | 422/88 |
| 2005/0056828 A1 | * | 3/2005 | Wada et al. | 257/40 |

* cited by examiner

*Primary Examiner*—Long V. Le
*Assistant Examiner*—Leon Y. Lum
(74) *Attorney, Agent, or Firm*—Quintero Law Office (57) ABSTRACT

The present invention relates to a structure and manufacturing process of a nano device transistor for a biosensor. The structure, the manufacturing process and the related circuit for a carbon nano tube or nano wire transistor biosensor device are provided. The refurbished nano device is used for absorbing various anti-bodies so as to detect the specific antigens or absorbing various biotins. Therefore, the object of the present invention to detect the specific species for bio measurement can be achieved.

12 Claims, 12 Drawing Sheets

STRUCTURE AND MANUFACTURING PROCESS OF A NANO DEVICE TRANSISTOR FOR A BIOSENSOR

BACKGROUND OF THE INVENTION

1. Field of the Invention

The present invention relates to a structure, manufacturing process and related circuit for a nano device transistor for a biosensor so as to achieve the object of detecting the specific species for bio measurement.

2. Description of the Prior Art

Figure 1:
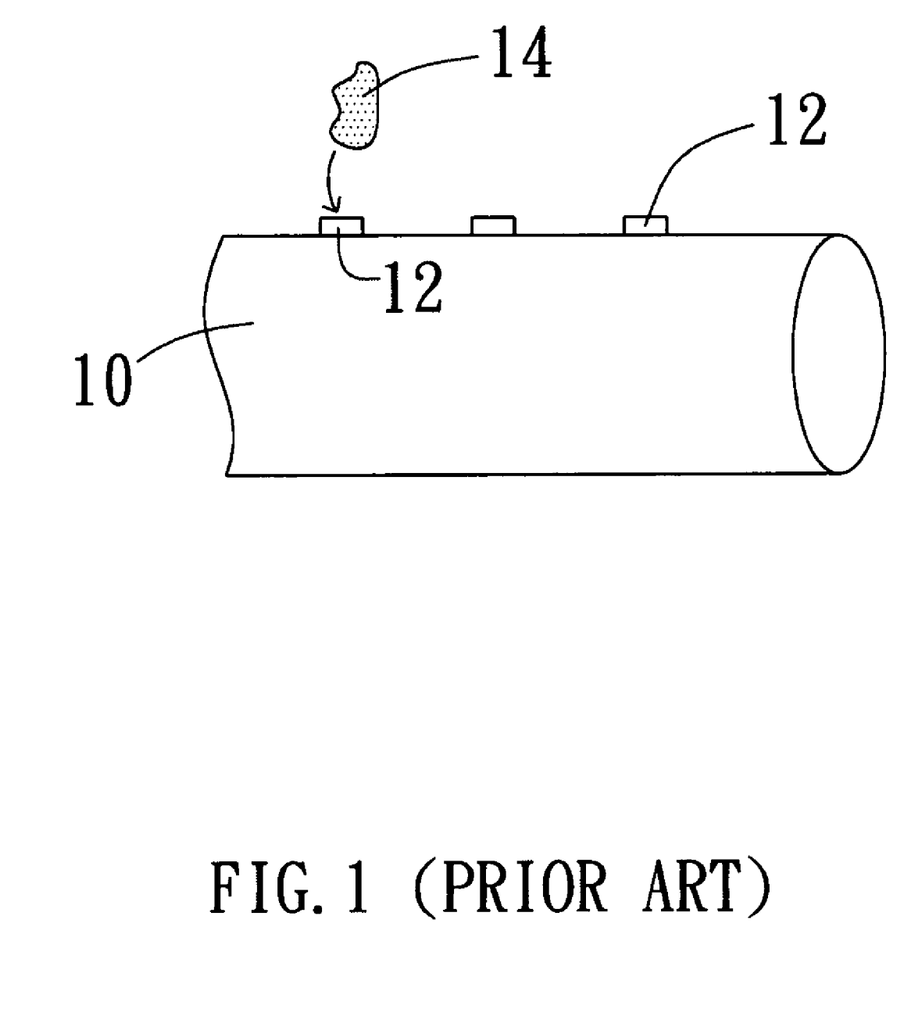
FIG. 1 is a perspective diagram of an anti-body and an antigen on the surface of the prior art nano wire.

In the journal of "Science" published in 2001, Professor Charles M. Lieber, the professor of the chemical department of Harvard university, published a paper related to the manufacturing of the biological and chemical sensor by using nano wire. As shown in FIG. 1, the refurbished nano wire 10 is used for absorbing different anti-bodies 12. After the antigen 14 and the anti-body 12 are combined and absorbed on the surface of the nano wire, the relative polarization (dipole) effect of the electric charges in the molecule on the nano wire 10 is equivalent to the effect of forming a fixed bias on the surface of the nano wire. This bias will affect the energy band of the nano wire so that the status of the current conduction will be varied. By sensing the variation of the status of the current conduction, it can be detected whether the specific antigen exist. In addition, by changing the anti-body 12 initially absorbed by the nano wire 10, the different kind of the antigen 14 can be detected.

Figure 2:
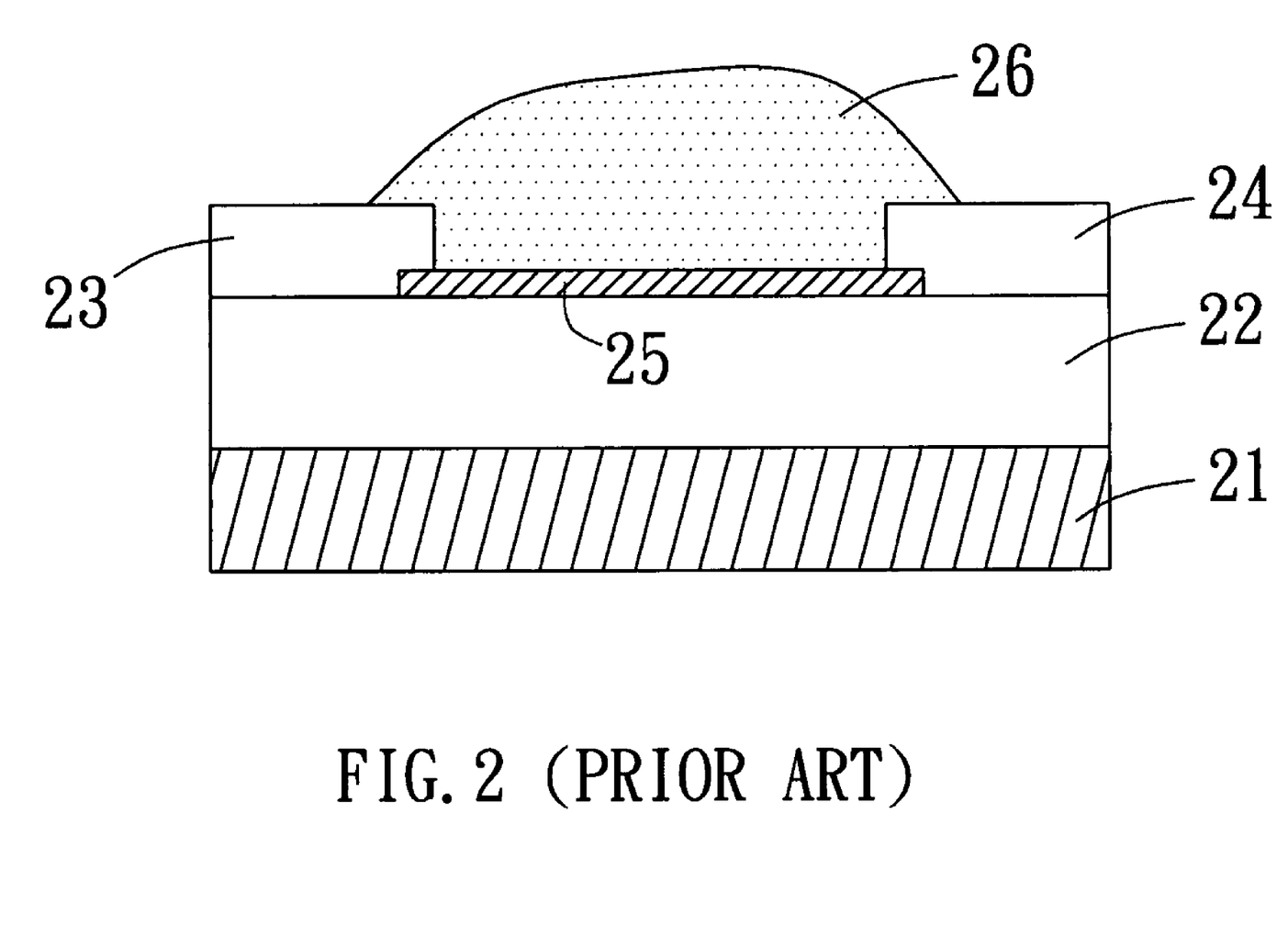
FIG. 2 is a perspective diagram of a structure of a prior art bio detection device.

FIG. 2 is the perspective diagram of a prior art device structure for bio measurement. An oxidization layer 22 for insulation is positioned on a silicon substrate 21, and metal drain 23 and source 24 capable of electric conduction are deposited on the oxidization layer 22. A nano channel layer 25 is deposited between the drain 23 and the source 24 for conducting the drain 23 and the source 24. When performing the bio measurement, the object 26 to be detected is dripped to be positioned on the source and drain 23, 24 and the nano channel layer 25, and a fixed bias effect is formed on the surface of the nano channel layer 25 so that the status of current conduction between the source and the drain will be varied.

Figure 3:
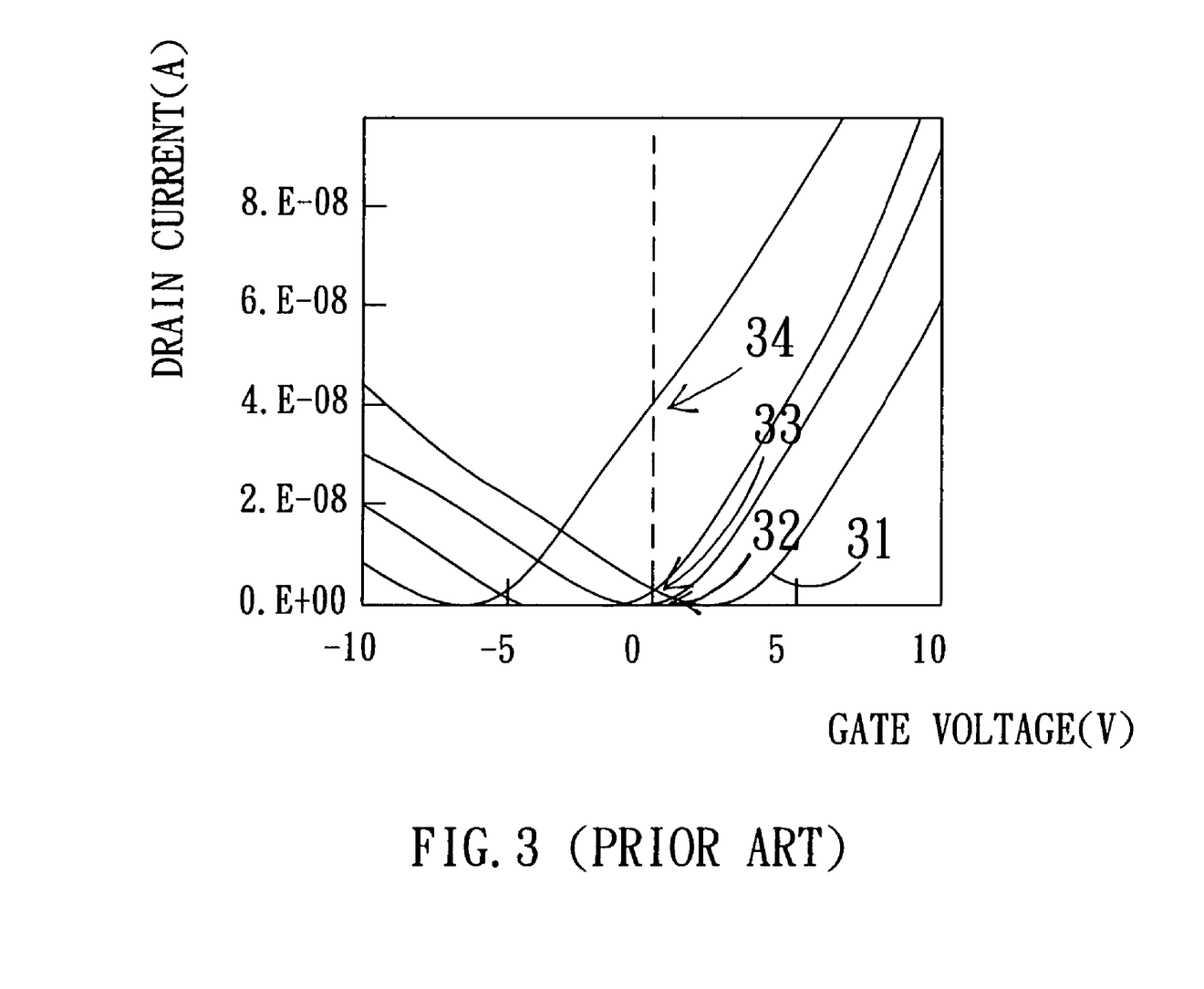
FIG. 3 is a voltage-current diagram of the prior art bio detection device.

Generally, the prior art carbon nano tube and nano wire transistor have the characteristic of two-way conduction (ambipolar). Under the different absorbing concentration of the bio object on the surface of the carbon nano tube and the nano wire, the bias level of the threshold conduction voltage will be different because of the different polarization effects of the electric charges. Please refer to FIG. 3. FIG. 3 is the prior art voltage-current diagram. The horizontal axis represents the gate voltage (V), and the vertical axis represents the variation of the current (I) during the detection. When the gate voltage is controlled to be 0V during detection, compared with the original conduction characteristic (as shown by the original curve 31) when not detecting, the practical existence of the object to be detected will affect the conduction characteristic of the carbon nano tube and the nano wire transistor, but because of the characteristic of two-way conduction, the current maybe less than (as the first position 32), equal to (as the second position 33), or greater than the original current (as the third position 34). Therefore, when the number of the bio objects to be detected, which are absorbed on the surface, the misjudgment is easily happened.

In order to resolve the possibility of the misjudgment, it is necessary to use a nano device transistor having the characteristic of one-way conduction. This object can be achieved by rigidly controlling the impurity doping concentration of the carbon nano tube and the nano wire. However, the dependence on the stability of the manufacturing process is too great, and it is not easy to control the uniformity of the practical impurity doping concentration. Therefore, the conduction characteristic of the device will be affected. Thus, the present invention provides the structure and the manufacturing process of a nano device transistor for a biosensor so as to achieve the characteristic of one-way conduction. By applying this structure, the correct judgment for the signals can be achieved.

Furthermore, in order to conveniently detect the different polarized electric charges after the different objects to be detected are absorbed on the nano channel layer 25, the nano device transistor having the conduction characteristics of the p-type and n-type semiconductors provides the greater flexibility of the detection method. However, under the atmosphere, the carbon nano tube and the nano wire presents the characteristic of the p-type semiconductor. In order to manufacture the carbon nano tube and the nano wire having the characteristics of the n-type semiconductor, the inside oxygen has to be effectively excluded. For example, the annealing under the vacuum, or using the solution of alkali metal ions to dope the carbon nano tube, or using the in-situ doping method to dope the nano wire, and so on. However, the above methods are not effective, and the results are not good. The conductive currents for the manufactured n-type semiconductor carbon nano tube and the nano wire transistor are not large. Therefore, the present invention provides a structure and manufacturing process for a double-gate carbon nano tube and nano wire transistor having the tunable voltage-controlled p-type or n-type conduction characteristics. Therefore, the object of p-type or n-type conduction can be achieved without modulating and controlling the manufacturing process.

Since the professor Charles M. Lieber published the article related to manufacture the bio and chemical sensor by using the nano wires, many researches are devoted to apply the carbon nano tube and the nano wire transistor to detect the different bio and chemical objects. However, the structure and circuit for the nano device transistor is not mentioned. Therefore, the present invention provides a structure and manufacturing process of a nano transistor for a biosensor so as to improve the correctness and the judgment of the detection and achieve the design of the p-type and n-type tunable conduction. The present invention provides the effective solution to resolve the problems of the prior art, and apply the serial connection or parallel connection structure of the nano device transistor for the biosensor to promote the sensitivity of the detection.

SUMMARY OF THE INVENTION

The present invention relates to a structure and manufacturing process of a nano device transistor for a biosensor. The structure, the manufacturing process and the related circuit for a nano device transistor for a biosensor are provided. The refurbished carbon nano tube and nano wire are used for absorbing various anti-bodies so as to detect the specific antigens or absorbing various biotins. Therefore, the object to detect the specific species for bio measurement can be achieved.

The manufacturing process comprises the following steps: depositing a bottom gate on a silicon substrate having $SiO_2$ deposited on it; depositing a gate oxidization layer to be an interface layer for insulating the bottom gate; coating a nano channel layer; depositing a metal electrodes on the nano channel layer and the gate oxidization layer, and performing coating, lithography, etching to form a drain and a source on the boundary of the nano channel layer and the gate oxidization layer; depositing a protection layer and performing the coating, lithography and wet etching to form a first protection layer and a second protection layer. The first protection layer and the second protection layer are used for separately covering and insulating the drain and the source, and an off-set area is defined on the boundary of the first protection layer and the second protection layer and the nano channel layer; and performing the lithography wet etching to define a detection area for detecting an object so as to achieve the object of the detecting the specific bio species for bio measurement.

BRIEF DESCRIPTION OF THE DRAWINGS

The accompanying drawings, which are incorporated in and form part of the specification in which like numerals designate like parts, illustrate preferred embodiments of the present invention and together with the description, serve to explain the principles of the invention. In the drawings.

DETAILED DESCRIPTION OF THE PREFERRED EMBODIMENT

Because the carbon nano tube and the nano wire device transistor for the bio and chemical sensor having the characteristic of the two-way conduction, the misjudgment will be easily caused when the number of the bio and chemical objects to be detected which are absorbed on the surface of the nano device are varied. Therefore, the present invention provides an off-set nano device transistor having the characteristic of one-way conduction. Even though the number of the bio objects to be detected which are absorbed on the surface of the nano device are different, the variation trend of the detection current varies in the same direction. This makes the misjudgment not easily happen.

Figure 4A:
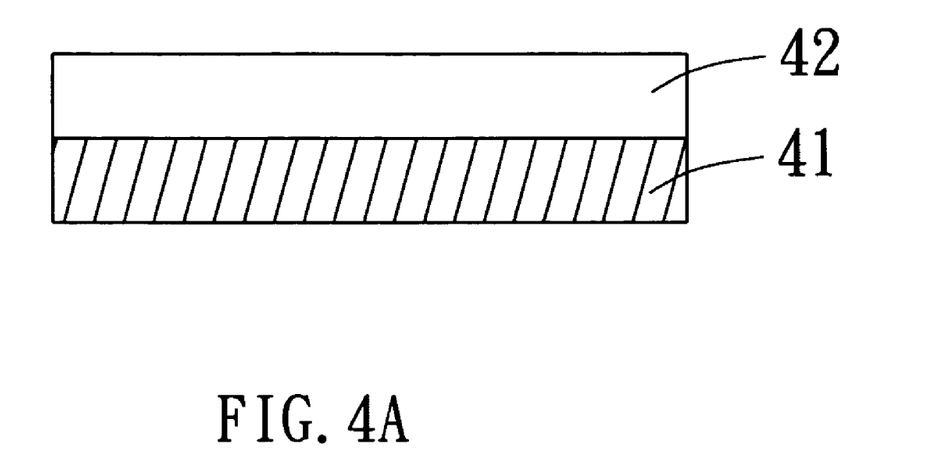
FIG. 4A to FIG. 4F are perspective diagrams for the manufacturing process of an off-set nano device transistor according to the present invention.
Figure 4B:
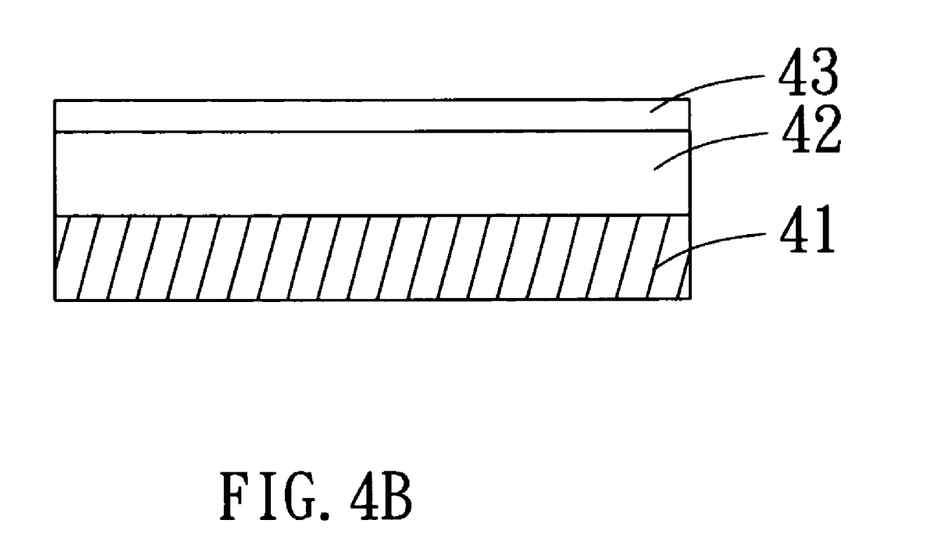
Figure 4C:
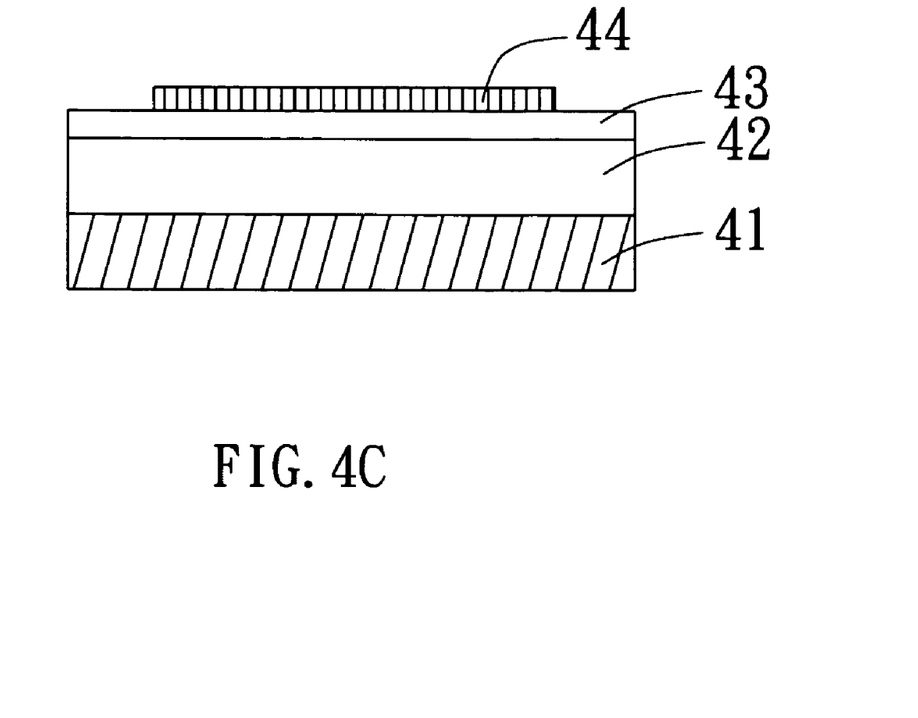
Figure 4D:
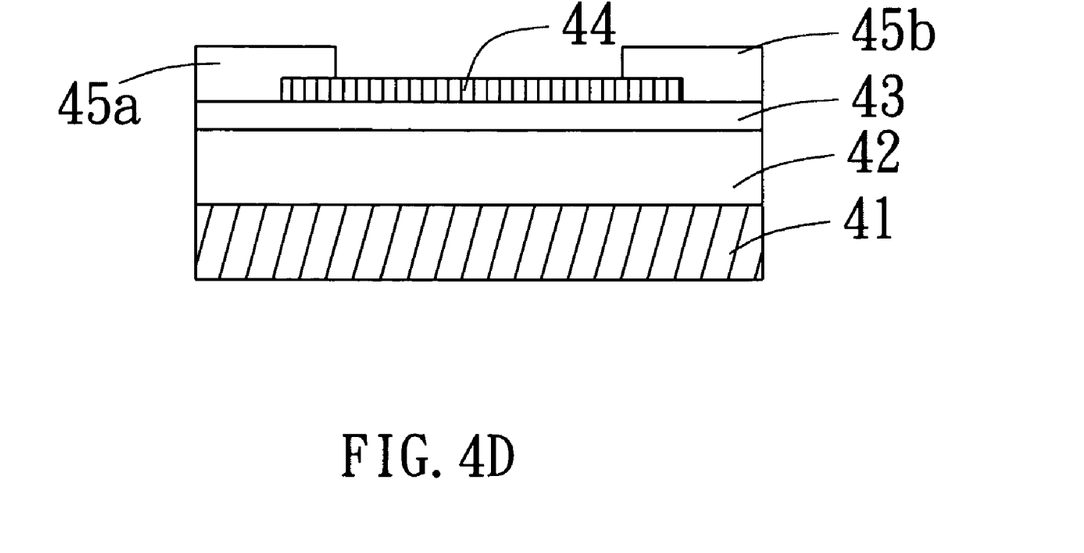
Figure 4E:
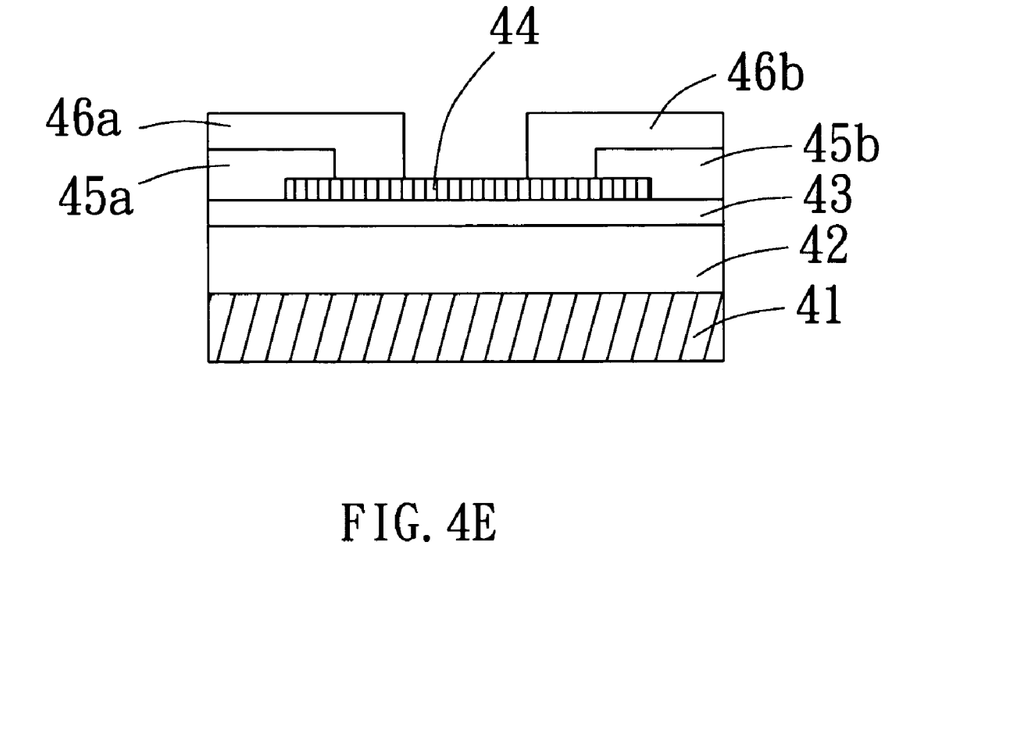
Figure 4F:
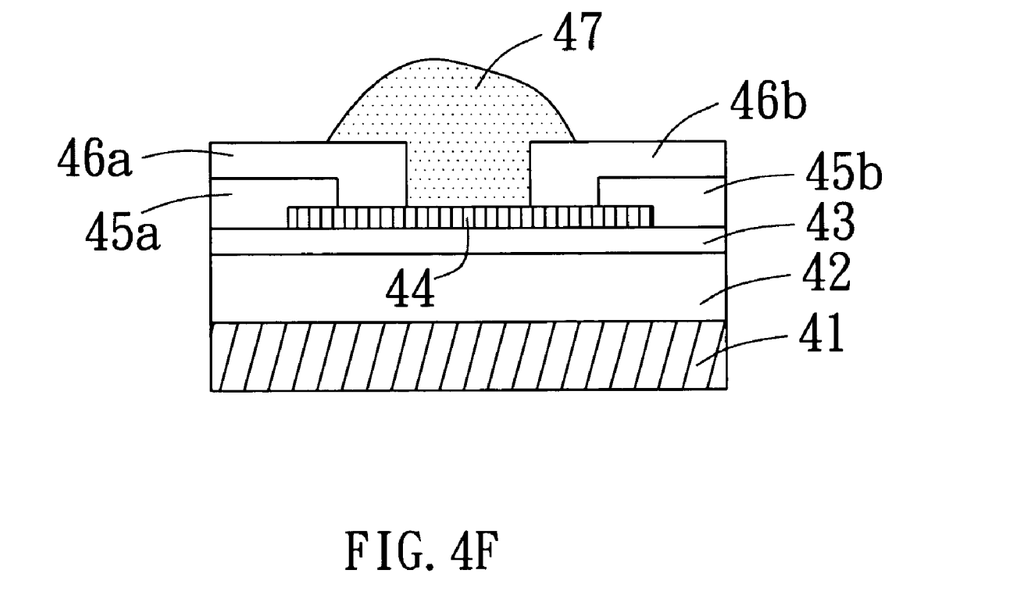

Please refer to FIG. 4A to FIG. 4F. FIG. 4A to FIG. 4F are perspective diagrams for the manufacturing process of an off-set nano device transistor. As shown in FIG. 4A, a bottom gate layer 42 is deposited on a silicon substrate 41 having $SiO_2$ deposited on it. This bottom gate layer 42 can be made of metal, poly-silicon, and so on, and the bottom gate layer 42 can be patterned by using a lithography etching method according to the practical requirements for the design. As shown in FIG. 4B, a gate dielectric layer 43 is deposited to be an interface layer for insulating the bottom gate 42. This gate dielectric layer 43 can be a dielectric layer made of the material of $SiO_x$, $SiN_x$ and so on, and the material is required not to be reacted with the surfactant, the anti-body and the antigen in chemical bonding. As shown in FIG. 4C, a nano channel layer 44 for the nano device is coated. As shown in FIG. 4D, the metal electrodes of drain 45a and source 45b made of metal material are formed between the boundary of the nano channel layer 44 and the gate oxidization layer 43. By applying the photo-resistant coating and the exposure lithography, the metal electrodes are patterned so as to define the upper area of the nano channel layer 44 and the areas of the drain 45a and the source 45b for the nano device. As shown in FIG. 4E, a protection layer made of the material of $SiO_x$ or $SiN_x$ is deposited above the areas of the drain 45a and the source 45b. This protection layer is made of the material which will not react with the surfactant, the anti-body and the antigen in chemical bonding. Then, by performing the coating, lithography, wet etching, the detection area is defined. As shown in the figure, after the etching, a first protection layer 46a and a second protection layer 46b are remained on the drain and the source for separately covering the drain 45a and the source 45b. In addition, an off-set area is formed on the joining portion of the first protection layer 46a, the second protection layer 46b and the nano channel layer 44. The final structure for the nano device transistor and the object 47 to be detected are shown in FIG. 4F. Before the object to be detected is dripped, the nano channel 44 is refurbished in advance so that the surfactant and the anti-body for the object to be detected are absorbed on the refurbished nano channel 44 for detecting the object. This object 47 to be detected is dripped on the off-set carbon nano tube and nano wire transistor device, and then is in touch with the protection layers 46a, 46b on the drain 45a and the source 45b for insulation, and also in touch with the nano channel layer 44.

In the mentioned structure, the nano device transistor controlled by the bottom gate 42 is accomplished, and the off-set area is formed. The existing of the off-set area makes this off-set nano device transistor having a better correctness and judgment. At the same time, because the two electrodes of the drain 45a and the source 45b are confined in the insulation layers (namely, the first protection layer 46a and the second protection layer 46b, the electrodes of the drain 45a and the source 45b are effectively prevented from chemically reacting with the object 47 to be detected in oxidization. Therefore, the drain 45a and the source 45b are not limited to be made of the material of inactive metal, and the short circuit problem caused by the source and drain 45a, 45b directly reacting with the bio-chemical solution can be avoided. The present invention forms a fixed bias effect on the surface of the nano channel layer 44, and the bias effect will affect the energy band of the nano channel layer 44 so that the status of current conduction will vary. By sensing the variation of the status of the current conduction, the existence of the specific antigen can be detected, and by changing the anti-body originally absorbed on the nano channel layer 44, the object of detecting different kinds of the antigens can be achieved.

Figure 6:
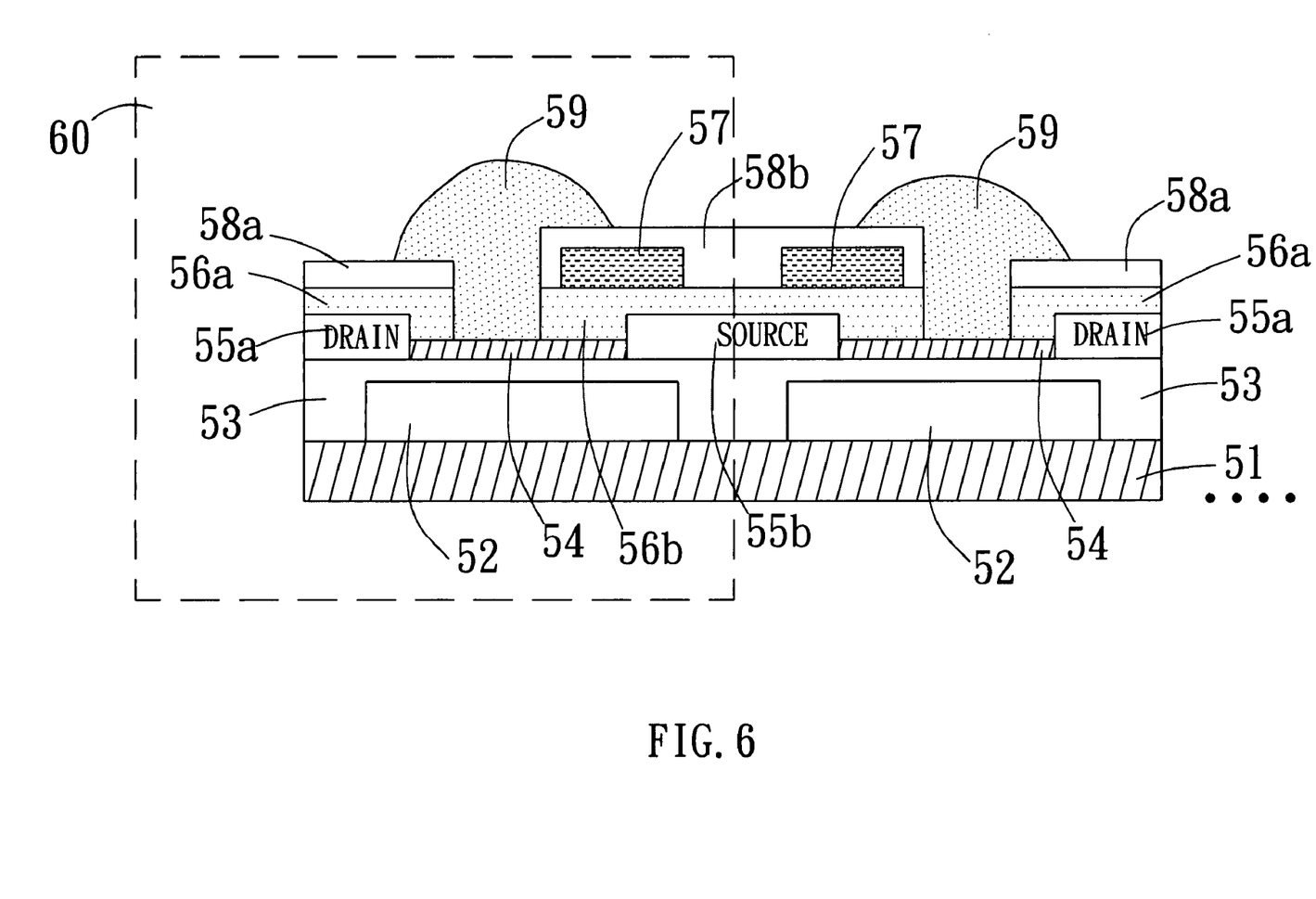
FIG. 6 is a perspective diagram of a serial connection structure of a nano device transistor for a biosensor according to the present invention.
Figure 7:
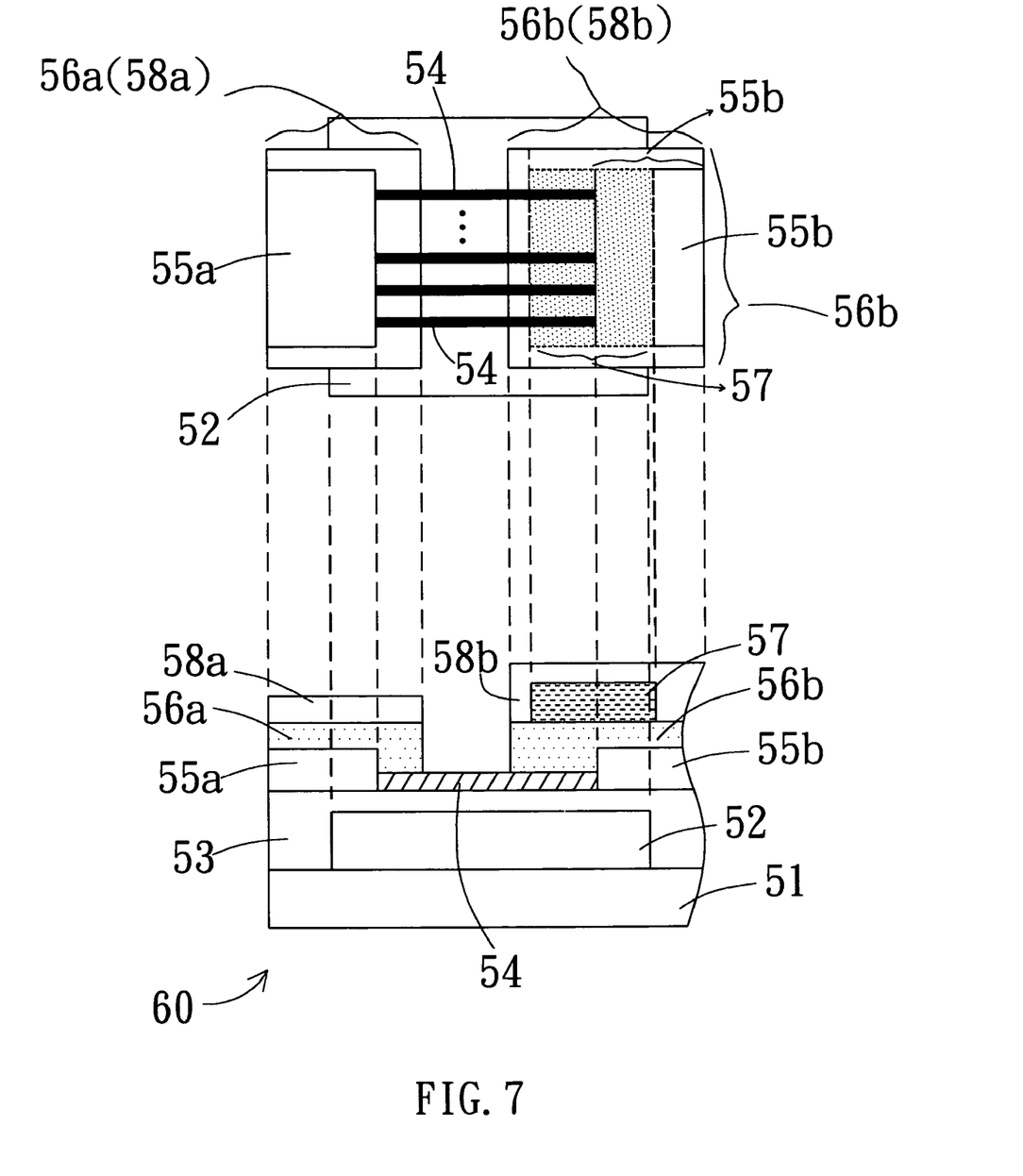
FIG. 7 is a perspective diagram of a parallel connection structure of a nano device transistor for a biosensor according to the present invention.

The present invention further applies a double gate device structure for manufacturing a bio-chemical sensor of a nano device transistor. This double gate structure can modulate the short gate bias based on requirements so as to form p-type and n-type carbon nano tube and nano wire transistor suitable to detect the bio-chemical object with various polarizations of electric charges. The structure also can be changed to be a serial connection structure and a parallel connection structure (as shown in FIG. 6 and FIG. 7), and the present invention is not limited to the method of controlling the doping concentration by using the manufacturing process to form the p-type and n-type carbon nano tubes and nano wire transistors.

Figure 5A:
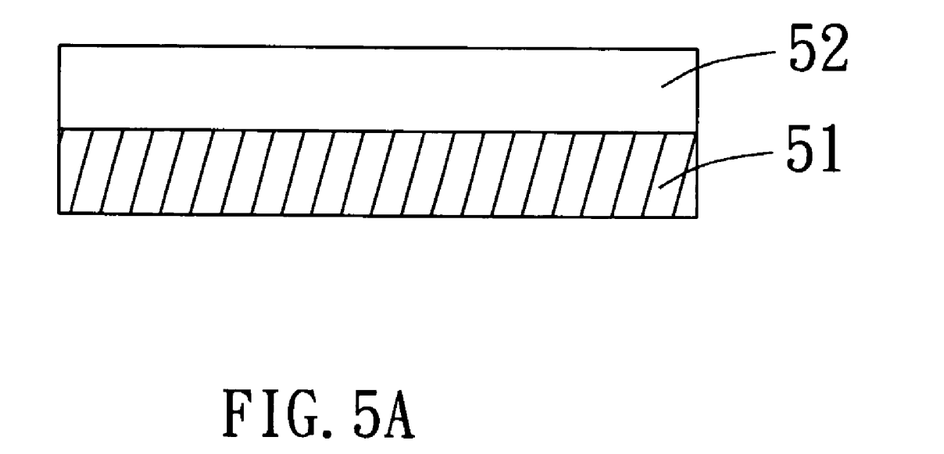
FIG. 5A to FIG. 5H are perspective diagrams for the manufacturing process of a double gate nano device transistor according to the present invention.
Figure 5B:
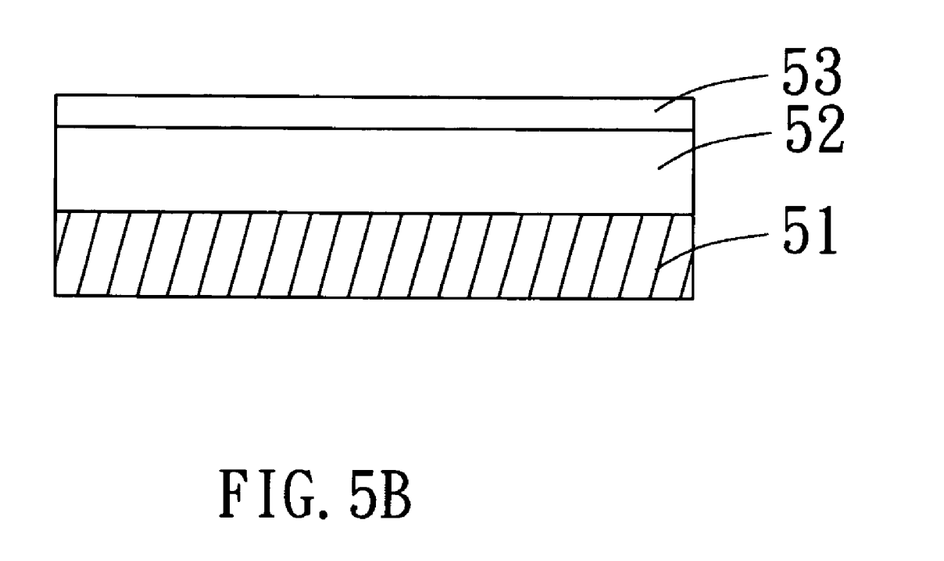
Figure 5C:
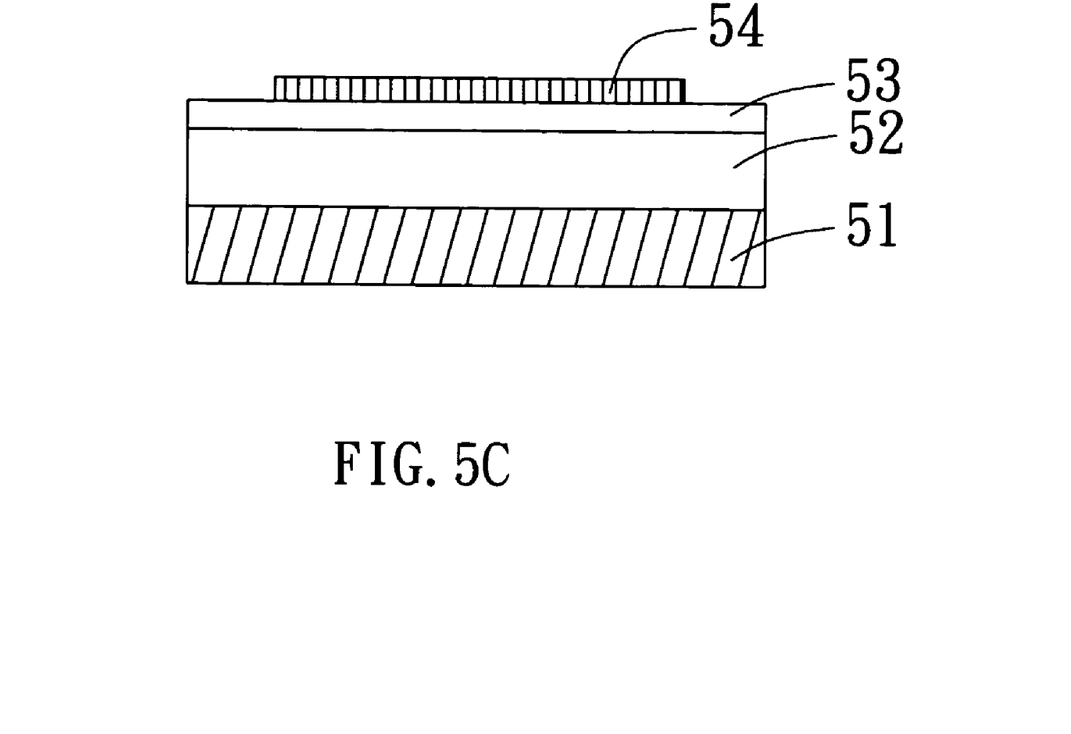
Figure 5D:
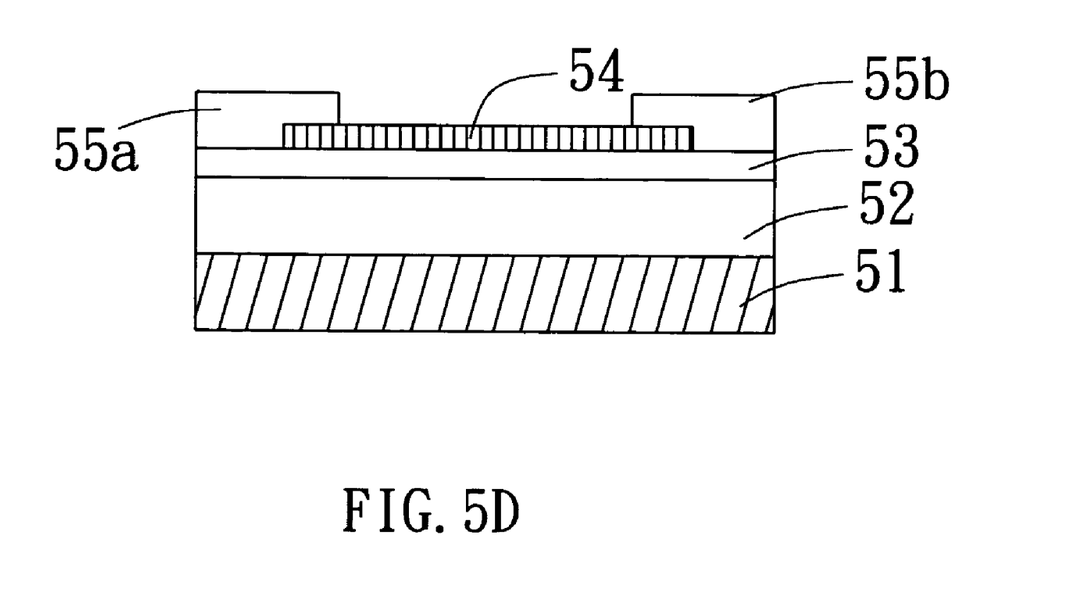

Please refer to FIG. 5A to FIG. 5H. FIG. 5A to FIG. 5H are perspective diagrams for the manufacturing process of a double gate nano device transistor according to the present invention. As shown in FIG. 5A, a bottom gate layer 52 is deposited on the silicon substrate 51 having $SiO_2$ deposited on it. This bottom gate 52 can be made of the material of metal, poly-silicon, and so on. According to the practical requirements for the design, the lithography etching method can be applied for patterning. As shown in FIG. 5B, a gate oxidization layer 53 is deposited to be a dielectric layer for insulating the bottom gate 52. The material of the layer 53 can be $SiO_x$ or $SiN_x$, which will not react with the surfactant, the anti-body and the antigen in chemical bonding. As shown in FIG. 5C, a nano channel layer 54 is coated for the nano device. As shown in FIG. 5D, the metal electrodes of the drain 55a and the source 55b are formed on the boundary of the nano channel layer 54 and the gate oxidization layer 53. By performing the photo-resistance coating and the exposure lithography, the metal electrodes 55a, 55b are patterned so as to define the upper area of the nano channel layer 54 and the areas of the drain 55a and the source 55b for the nano device.

Figure 5E:
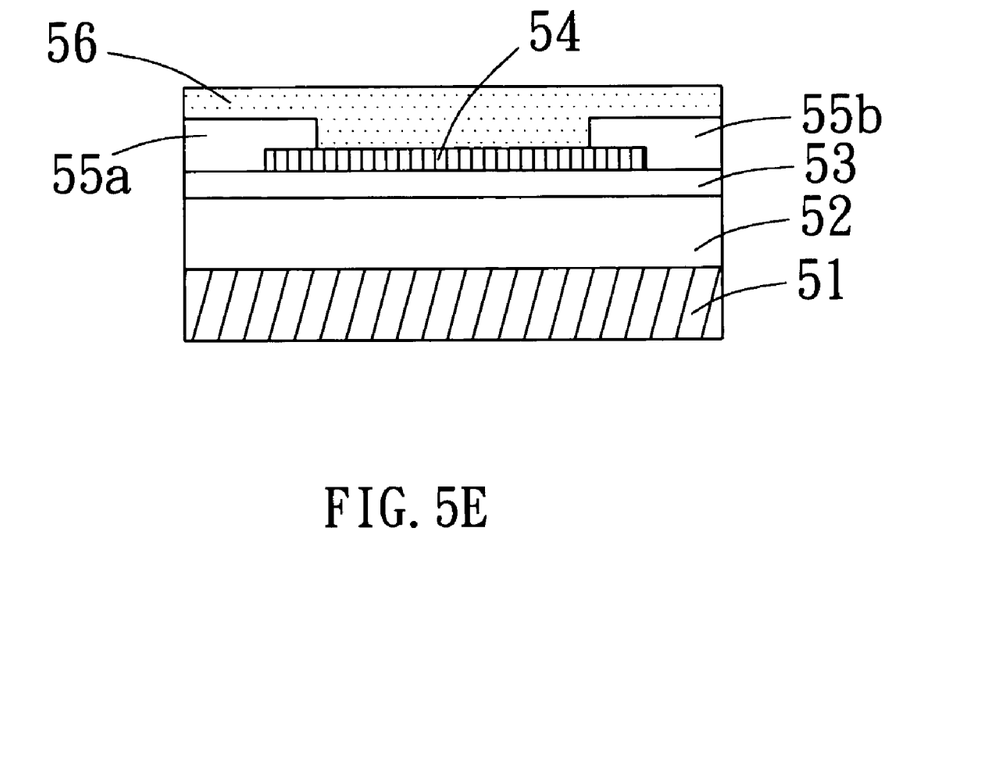
Figure 5F:
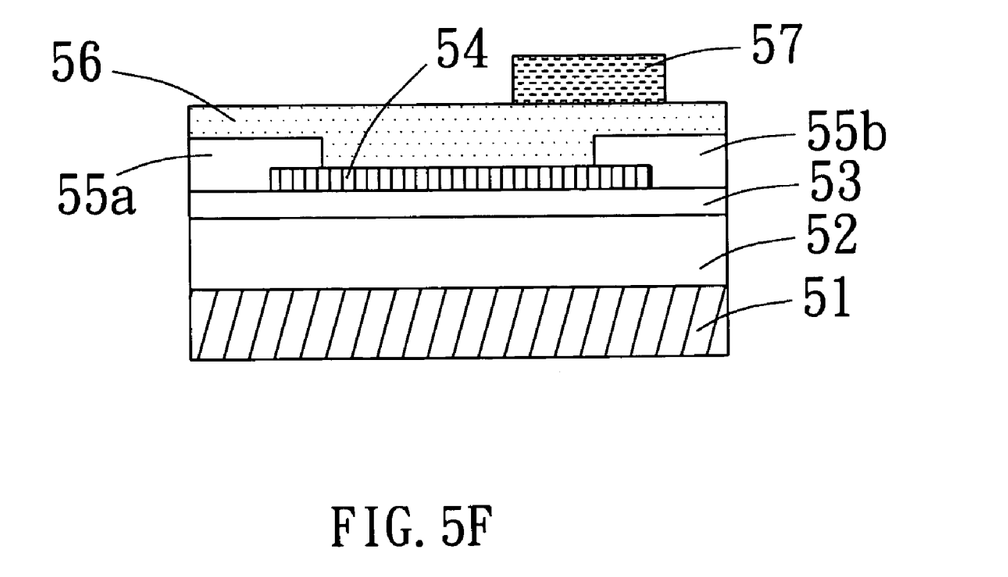
Figure 5G:
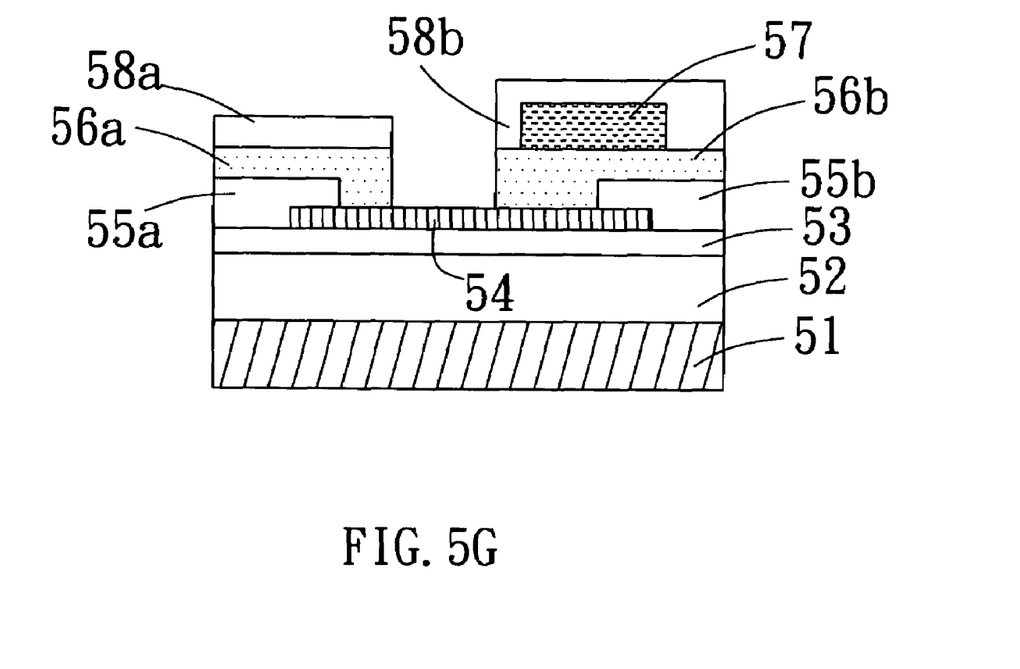
Figure 5H:
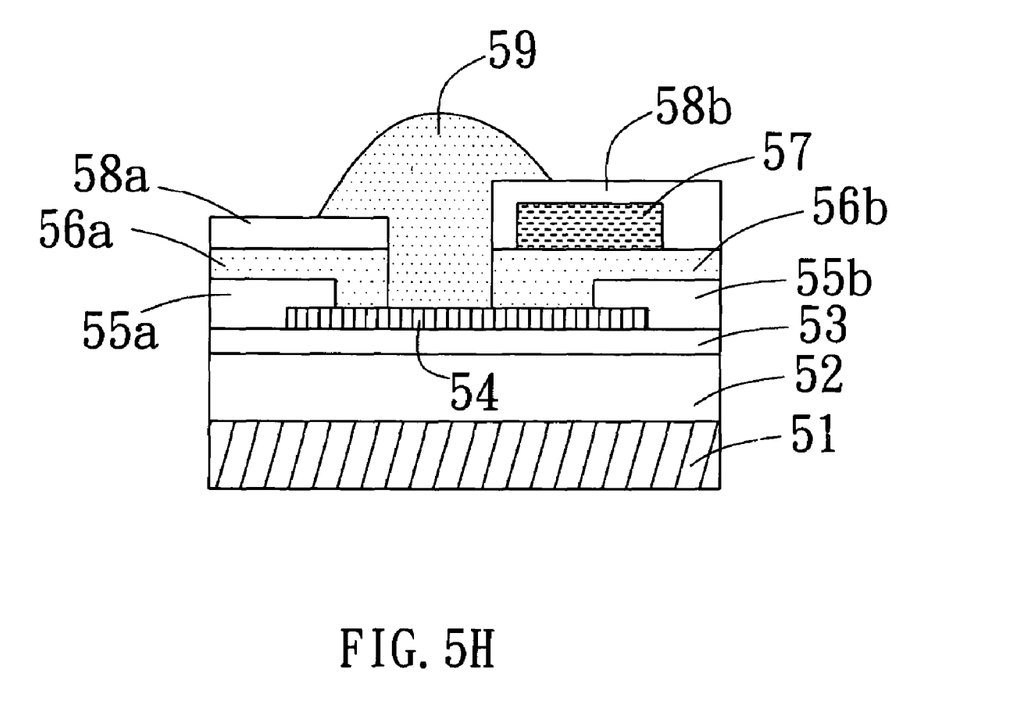

As shown in FIG. 5E, a ceiling gate dielectric layer 56 is deposited for insulating the drain 55a, the source 55b and the nano channel layer 54 from the device above the nano device transistor. As shown in FIG. 5F, a layer of ceiling gate 57 made of metal material is deposited on the ceiling gate dielectric layer 56, and the lithography etching method is applied to define the shape of the ceiling gate 57. The position of the ceiling gate 57 can be any position on the ceiling gate dielectric layer 56, and the ceiling gate 57 covers a portion of the nano channel layer 54. As shown in FIG. 5G, after a protection layer deposited, the lithography etching method is performed to etch downward the protection layer and the ceiling gate dielectric layer 56 by wet etching (FIG. 5F) so as to form the first ceiling gate dielectric layer 56a and the second ceiling gate dielectric layer 56b. The first protection layer 58a and the second protection layer 58b cover the surfaces of the ceiling gate dielectric layers 56a, 56b positioned at two sides so as to define and form a hollowing detection area for detecting the bio object. As shown in FIG. 5H, the object 59 to be detected is in touch with the nano channel layer 54 of the detection area.

Therefore, the double gate nano device transistor is accomplished. When performing the detection for the bio object, the bio object (antigen) is dripped on the uncovered area of the nano device (such as the nano channel layer) When there is an antigen matching with the anti-body on the surface of the nano device, the antigen will be absorbed and fixed on the nano device so as to produce the polarization effect of the electric charges. This will cause the variation of the energy band of the nano device.

The structure and manufacturing process of the nano device transistor for the biosensor according to the present invention is suitable for detecting the bio-chemical objects with various polarizations of electric charges, and the structure can be changed to be the serial connection structure and the parallel connection structure. Furthermore, the present invention is not limited to the method of controlling the doping concentration by using the manufacturing process to form the p-type and n-type carbon nano tubes and nano wire transistors. The following is the description for the serial and parallel connection structures.

Please refer to FIG. 6. FIG. 6 is a perspective diagram of a serial connection structure of a nano device transistor for a biosensor according to the present invention. The nano device transistors 60 manufactured by the manufacturing process shown in FIG. 5A to FIG. 5H are serially connected to form a serial connection structure of a double gate nano device transistor. As shown in FIG. 6, the two portions of the structure are symmetrical along the source 55b. Two bottom gates 52 are separately deposited on the silicon substrates 51 having deposited $SiO_2$ for the nano device transistors 60. The bottom gates 52 can be made of the material of metal, poly-silicon, and so on. According to the practical requirements for the design, the lithography etching method is performed for patterning. The bottom gates 52 are surrounded and confined by the gate dielectric layers 53 so as to insulating the bottom gates 52 from the outside. The gate dielectric layers 53 can be made of the material of $SiO_x$ or $SiN_x$, which will not react with the surfactant, the anti-body and the antigen in chemical bonding. The drain 55a and the source 55b of the nano device transistor 60 are positioned on the gate dielectric layer 53, and the nano channel layer 54 is coated between the drain 55a and the source 55b. The nano channel layer 54 is made of the nano material, the carbon nano tube or the nano wire.

A first ceiling gate dielectric layer 56a and a second ceiling gate dielectric layer 56b are deposited on the drain 55a and the source 55b for insulating the drain 55a, the source 55b and the nano channel layer 54 from the device on the nano device transistor 60. A ceiling gate 57 made of metal material is further deposited on the ceiling gate dielectric layer for being the electrode of the nano device transistor 60. The position of the ceiling gate 57 can be any position on the ceiling gate dielectric layers 56a, 56b, and the ceiling gate 57 covers a portion of the nano channel layer 54. On the surfaces of the ceiling gate dielectric layer 56a and the second ceiling gate dielectric layer 56b, the first protection layer 58a and the second protection layer 58b separately form the hollowing detection area for detecting the bio object. Finally, the object 59 to be detected is in touch with the nano channel layer 54 of the detection area, and the first protection layer 58a and the second protection layer 58b will insulate the electrode in the device so as to avoid the short circuit between the electrodes caused by the electric ions in the object 59 to be detected.

As for sensitivity of the detection for the bio object by the nano device transistor biosensor, it is related to the number of the bio objects bonded on the surface of the nano device, such as the carbon nano tube or the nano wire, and therefore, in order to increase the sensitivity of the detection, the serial connection structure can be applied to increase the touching area of the nano device. Furthermore, when the object 59 to be detected exists, the status of the sensor will be changed from "ON" to "OFF". In addition, the serial connection structure of the nano device transistor 60 can be used for increasing the sensitivity.

Furthermore, a plurality of off-set nano device transistors made by the manufacturing process shown in FIG. 4A to FIG. 4F also can be connected to form a serial connection structure of the off-set nano device transistors.

FIG. 7 is a perspective diagram of a parallel connection structure of a nano device transistor for a biosensor according to the present invention. A plurality of nano channel layers 54 are connected between the drain 55a and the source 55b in the structure of the double gate nano device transistor so as to form a parallel connection structure of the double gate nano device transistor. FIG. 7 presents a top view of the nano device transistor 60 in parallel connection structure. A plurality of nano channel layers 54 are connected in parallel between the drain 55a and the source 55b. Under them, there is a bottom gate 52, and a first ceiling gate dielectric layer 56a and a second ceiling gate dielectric layer 56b cover on the drain 55a and the source 55b. A ceiling gate 57 is positioned on the second ceiling gate dielectric layer 56b, and the protection layers 58a, 58b for insulation are separately positioned on the first ceiling gate dielectric layer 56a and the second ceiling gate dielectric layer 56b. Besides, when the object 59 to be detected exists so as to make the status of the sensor changed from "OFF" to "ON", the parallel connection structure of the nano device transistor 60 can be used for increasing the sensitivity. This parallel connection structure also can be realized by using an external circuit to connect the drains 55a and the sources 55b of the plurality of double gate nano device transistors. By applying the parallel connection structure or the serial connection structure, the sensitivity of the detection for the bio object can be increased.

Similarly, a parallel connection structure of the off-set nano device transistor can be realized by connecting a plurality nano channel layers 54 in the structure of the off-set nano device transistor produced by the manufacturing process shown in FIG. 4A to FIG. 4F. Furthermore, the parallel connection structure also can be realized by connecting a plurality of off-set nano device transistors made by the manufacturing process shown in FIG. 4A to FIG. 4F.

The above is the detailed description of the structure and manufacturing process of the nano device transistor for the biosensor according to the present invention. This structure applies the off-set, double gate together with the serial connection and parallel connection structures so as to achieve the object of detecting the specific bio species for bio measurement.

Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A structure of a nano device transistor for a biosensor, comprising:
   a silicon substrate having $SiO_2$ deposited thereon;
   a bottom gate positioned on the silicon substrate having $SiO_2$ deposited thereon;
   a gate dielectric layer positioned on the bottom gate being an interface layer for insulating the bottom gate;
   a nano channel layer positioned on the gate dielectric layer;
   a drain positioned extending over a first portion of a top surface of the nano channel layer and a first portion of a top surface of the gate dielectric layer;
   a source positioned extending over a second portion of the top surface of the nano channel layer and a second portion of the top surface of the gate dielectric layer;
   a ceiling gate dielectric layer comprising a first ceiling gate dielectric layer portion and a second ceiling gate dielectric layer portion positioned on the drain and the source, respectively;
   a ceiling gate positioned on the ceiling gate dielectric layer;
   a first protection layer positioned on the first ceiling gate dielectric layer portion; and
   a second protection layer positioned on the second ceiling gate dielectric layer portion.

2. The structure of claim 1, wherein the bottom gate comprises metal or poly-silicon.

3. The structure of claim 1, wherein a surfactant and a target anti-body are absorbable on the nano channel layer.

4. The structure of claim 1, wherein the drain and the source are metal electrodes.

5. The structure of claim 1, wherein the first protection layer and the second protection layer comprise silicon oxide, silicon nitride or other insulation materials.

6. The structure of claim 1, wherein the gate dielectric layer comprises silicon oxide, silicon nitride or other gate dielectric materials.

7. The structure of claim 1, wherein the ceiling gate comprises metal.

8. The structure of claim 1, wherein the first ceiling gate dielectric layer portion and the second ceiling gate dielectric layer portion comprise silicon oxide, silicon nitride or other insulation materials.

9. The structure of claim 1, wherein the ceiling gate covers a portion of the nano channel layer.

10. The structure of claim 1, wherein a plurality of the nano device transistors are connected to form a serial connection structure of the nano device transistors.

11. The structure of claim 1, wherein a plurality of the nano channel layers are connected between the drain and the source in the nano device transistor, or a plurality of the nano device transistors are connected to form a parallel connection structure for the nano device transistor.

12. The structure of claim 1, wherein the first protection layer, the second protection layer and the nano channel layer are used for defining a detection area.

* * * * *